United States Patent
Yamaguchi (10) Patent No.: US 11,282,686 B2
(45) Date of Patent: Mar. 22, 2022

(54) IMAGING MASS SPECTROMETER

(71) Applicant: SHIMADZU CORPORATION, Kyoto (JP)

(72) Inventor: Shinichi Yamaguchi, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 91 days.

(21) Appl. No.: 16/959,457

(22) PCT Filed: Feb. 5, 2018

(86) PCT No.: PCT/JP2018/003758
§ 371 (c)(1),
(2) Date: Jul. 1, 2020

(87) PCT Pub. No.: WO2019/150574
PCT Pub. Date: Aug. 8, 2019

(65) Prior Publication Data
US 2021/0384020 A1    Dec. 9, 2021

(51) Int. Cl.
*H01J 49/04* (2006.01)
*H01J 49/00* (2006.01)
*G01N 27/62* (2021.01)

(52) U.S. Cl.
CPC ............ *H01J 49/004* (2013.01); *G01N 27/62* (2013.01); *H01J 49/0036* (2013.01)

(58) Field of Classification Search
CPC ............... H01J 49/0004; H01J 49/0036; H01J 49/0031; G01N 27/62; G01N 21/65
(Continued)

(56) References Cited

U.S. PATENT DOCUMENTS

| 8,384,021 B2 * | 2/2013 | Komatsu | G16B 45/00 |
| | | | 250/282 |
| 2018/0024108 A1 * | 1/2018 | Cooks | G01N 33/487 |
| | | | 250/282 |

(Continued)

FOREIGN PATENT DOCUMENTS

| JP | 2013-40808 A | 2/2013 | |
| JP | 2013040808 A * | 2/2013 | ............. G16C 20/20 |

OTHER PUBLICATIONS

"iMScope TRIO imaging mass microscope", Shimadzu Corporation, the Internet http://www.an.shimadzu.co.jp/bio/imscope/, accessed on Apr. 3, 2017, 7 pages.

(Continued)

*Primary Examiner* — Michael Maskell
(74) *Attorney, Agent, or Firm* — Sughrue Mion, PLLC (57) ABSTRACT

A user enters structures of a plurality of metabolite candidates contained in a sample. A dissociation pattern predictor predicts a dissociation pattern for each metabolite candidate. An MS/MS spectrum estimator estimates an MS/MS spectrum and stores it in a teaching data storage. An imaging mass spectrometry unit acquires measured MS/MS spectra for each measurement point within a measurement range on a sample by performing an MS/MS analysis in which a precursor ion based on mass information of each metabolite candidate is used as an analysis target. A multivariate analysis processor performs a multivariate analysis in which the peak information based on the MS/MS spectra stored in the teaching data storage is used as teaching data, to classify measured MS/MS spectra at each measurement point into a plurality of metabolite candidates. Based on the classification result, a spatial distribution creator creates an image showing a spatial distribution for each metabolite candidate.

4 Claims, 3 Drawing Sheets

(58) Field of Classification Search
USPC .................................................. 250/281, 282
See application file for complete search history.

(56) References Cited

U.S. PATENT DOCUMENTS

2018/0197726 A1* 7/2018 Yamaguchi ............ G16B 40/30
2021/0020420 A1* 1/2021 Yamaguchi ......... H01J 49/0036

OTHER PUBLICATIONS

"ACD/MS Fragmenter—Predict Mass Spectral Fragmentation", Advanced Chemistry Development, Inc., the Internet http://www.acdlabs.com/products/adh/ms/ms_frag/, accessed on Apr. 3, 2017, 2 pages.
International Search Report for PCT/JP2018/003758 dated Apr. 17, 2018.
Written Opinion of the International Searching Authority for PCT/JP2018/003758 dated Apr. 17, 2018.

* cited by examiner

Fig. 1

IMAGING MASS SPECTROMETER

CROSS-REFERENCE TO RELATED APPLICATIONS

This application is a National Stage of International Application No. PCT/JP2018/003758 filed Feb. 5, 2018, the disclosure of which is incorporated herein in its entirety by reference.

TECHNICAL FIELD

The present invention relates to an imaging mass spectrometer capable of an $MS^n$ analysis (where n is an integer equal to or greater than two) for each measurement point within a two-dimensional measurement area on a sample.

BACKGROUND ART

Pharmacokinetic studies are a type of study primarily aimed at investigating absorption, distribution, metabolism, elimination and other phases of a test drug administered to human subjects or laboratory animals. One of the particularly important items of information obtained through this study is the body distribution of drug metabolites. A conventionally and commonly used technique for investigating the spatial distribution of a metabolite is to label the administered drug with a radioactive isotope (radioisotope labelling: RI) and take an image of a biological tissue after the drug administration using a two-dimensional detector (autoradiography). This technique enables estimation of the position and quantity of the metabolite. However, it is naturally impossible to obtain information concerning the molecular structure of the metabolite.

In recent years, it has become possible to measure a two-dimensional intensity distribution of an ion having a specific mass-to-charge ratio m/z on a sample, such as a biological tissue section, by a mass spectrometric imaging method using an imaging mass spectrometer, one example of which is disclosed in Non Patent Literature 1. Meanwhile, to date, various metabolic pathways have been revealed, and it has become possible to estimate a possible structure of a metabolite (metabolite candidate) with a high level of accuracy based on the information concerning such metabolic pathways and the structural information of the drug. By performing an imaging mass spectrometric analysis in which the mass-to-charge ratio calculated from the estimated metabolite candidate is designated as the target, the spatial distribution of the metabolite can be visualized.

However, in the case of a biological tissue section or similar sample of biological origin, various substances commonly contained in biological tissues possibly may obstruct the detection of the target substance, such as a metabolite. As a means for solving such a problem, imaging mass spectrometry employing the technique of MS/MS analysis (or $MS^n$ analysis with n being equal to or greater than three) has been used.

For example, an imaging mass spectrometer described in Patent Literature 1 performs an imaging mass spectrometric analysis employing an MS/MS analysis in order to distinguish between an ion originating from a target compound and an ion originating from a foreign substance whose mass-to-charge ratio is close to that of the target ion. A reference ion which originates from the target compound is selected from product-ion spectra respectively acquired at the measurement points, and a product ion is extracted which has a different mass-to-charge ratio and yet shows a spatial distribution similar to the reference ion. A combination of the precursor ion and the product ion is formed, and the process of identifying the target compound from the combination and estimating its composition is performed for this combination. Since the specificity of the compound to be detected is improved by the use of the MS/MS analysis, this imaging mass spectrometer can accurately determine the spatial distribution of the target compound even under the condition where a foreign substance whose mass is close to that of the target compound is present.

Such a type of conventional imaging mass spectrometer basically provides users with a mass spectrometric imaging graphic which shows the spatial intensity distribution of an ion having a specific mass-to-charge ratio, or spatial intensity distribution of an ion resulting from a specific combination of the mass-to-charge ratio of the precursor ion and that of the product ion. However, a compound may have structural isomers which are approximately identical in mass-to-charge ratio and yet differ from each other in structure. A metabolite often has a comparatively large number of structural isomers. Such structural isomers cannot be distinguished from each other in the spatial intensity distribution of the ion acquired for each mass-to-charge ratio in the previously described manner. Therefore, in some cases, the spatial distribution information of the compound cannot be correctly determined. The use of an MS/MS analysis allows for the distinction between structural isomers. However, the technique used in the device described in Patent Literature 1 merely provides the spatial intensity distribution of a compound having a specific structural isomer. It is impossible to acquire the spatial intensity distribution for each compound having a different structure.

CITATION LIST

Patent Literature

Patent Literature 1: JP 2013-40808 A

NON PATENT LITERATURE

Non Patent Literature 1: "iMScope TRIO Imeejingu shisuryou Kenbikyou (iMScope TRIO imaging mass microscope)", Shimadzu Corporation, [online], [accessed on Apr. 3, 2017], the Internet Non Patent Literature 2: "ACD/MS Fragmenter—Predict Mass Spectral Fragmentation", Advanced Chemistry Development, Inc., [online], [accessed on Apr. 3, 2017], the Internet

SUMMARY OF INVENTION

Technical Problem

The present invention has been developed to solve the previously described problem. Its primary objective is to provide an imaging mass spectrometer capable of determining a spatial distribution of each compound in the case where a plurality of kinds of compounds which are exactly or substantially identical in mass and yet different from each other in structure.

Solution to Problem

The present invention developed for solving the previously described problem is an imaging mass spectrometer equipped with a measurement section capable of performing an MS$^n$ analysis (where n is an integer equal to or greater than two) for each of a plurality of measurement points set within a two-dimensional area on a sample, the imaging mass spectrometer including:

a) a reference spectrum acquirer configured to acquire reference product-ion spectra which respectively correspond to a plurality of compound candidates;

b) an analysis controller configured to control the measurement section so as to perform MS$^n$ analyses corresponding to the mass-to-charge ratios of the plurality of compound candidates and collect spectrum data for each measurement point within a measurement area on a sample;

c) a spectrum classifier configured to classify measured product-ion spectra obtained under the control of the analysis controller, by a multivariate analysis in which a plurality of reference product-ion spectra acquired by the reference spectrum acquirer are used as teaching data; and     d) an image creator configured to determine information of the spatial distribution of each compound candidate based on a classification result obtained by the spectrum classifier, and create an image visualizing the spatial distribution.

In the imaging mass spectrometer according to the present invention, the reference spectrum acquirer acquires reference product-ion spectra which respectively correspond to a plurality of compound candidates which, for example, are specified by the user. Specifically, for example, the reference spectrum acquirer can acquire reference product-ion spectra by reading product-ion spectra corresponding to the compound candidates from a library of product-ion spectra prepared in the form of a database based on the results of actual measurements conducted beforehand for a considerable number of compounds.

The reference spectrum acquirer may be configured to estimate the pattern of the dissociation of the ion for each compound candidate based on the structures of the plurality of compound candidates, and determine theoretical product-ion spectra to be obtained through the dissociation. According to this configuration, for example, a user specifies, from an input unit, the structures of a plurality of compound candidates which are considered to be contained in the sample, or those which need to be observed. Based on the structures of the specified compound candidates, the reference spectrum acquirer estimates the pattern of the dissociation of the ion in an MS$^n$ analysis for each compound candidate, i.e. the product ions to be generated through the dissociation, and determines a theoretical product-ion spectrum. Once the ion dissociation technique (e.g. the collision induced dissociation or electron capture ionization) and dissociation conditions (e.g. the dissociation energy in the case of the collision induced dissociation) have been determined, the dissociation pattern can be estimated. There are commonly known techniques for the estimation. Understandably, such theoretical product-ion spectra can be previously compiled into a database.

The analysis controller acquires spectrum data for each measurement point within a measurement area by controlling the measurement section so as to perform an MS$^n$ analysis in which the ions corresponding to the mass-to-charge ratios of the plurality of compound candidates, i.e. the ions originating from those compound candidates, are each used as the precursor ion, and to acquire spectrum data for each measurement point. A typical value of n is two, although it may be three or more. For example, if all of the compound candidates have the same mass, an MS/MS analysis for a precursor ion having the same mass-to-charge ratio (product-ion scan measurement) is performed. If those compound candidates have different masses, the mass-to-charge ratio of the precursor ion originating from each compound candidate normally varies from candidate to candidate, and therefore, a set of MS/MS analyses for a plurality of different precursor ions is performed for each measurement point.

After the measured product-ion spectra have been obtained by a measurement in the previously described manner, the spectrum classifier performs a multivariate analysis according to a predetermined algorithm in which a plurality of reference product-ion spectra acquired by the reference spectrum acquirer are used as teaching data, to classify the measured product-ion spectra. For this purpose, various types of multivariate analyses are available which can perform supervised classification, i.e. classification with an objective variable. As typical examples, the partial least squares (PLS), correlation analysis method, discrimination analysis, hierarchical cluster analysis (HCA) and k-means cluster analysis are useful.

Since a product-ion spectrum reflects the structure of a compound, the aforementioned classification of the spectra has the same meaning as the classification of the compound candidates according to their structural similarity or difference. Therefore, if there are measurement points at which product-ion spectra classified into the same class (group) have been acquired, it is possible to consider that the same compound candidate corresponding to that class of product-ion spectra is present at all of those measurement points. Based on the classification result, the image creator determines information on the spatial distribution of each compound candidate and creates an image which visualizes the spatial distribution. Thus, an image visualizing the spatial distribution can be acquired for each of the plurality of compound candidates.

This spatial distribution may include intensity information reflecting the abundance of the compound candidate, or it may be a spatial distribution which does not contain intensity information but merely shows the ranges in which the compound candidate is present. The intensity information of the compound candidate can be obtained, for example, based on the intensity value of the peak having the highest intensity in the product-ion spectrum, or an accumulated value of the intensities of all ions observed on the spectrum (i.e. the so-called total ion chromatogram, or TIC).

In the imaging mass spectrometer according to the present invention, the determination of a measurement point at which a compound candidate is present (or in other words, the identification of a compound candidate present at a measurement point) is primarily based on the product-ion spectrum. However, if a piece of information concerning the distribution of the compound in the sample in question has been obtained by a measurement technique or observation technique other than mass spectrometry, such information can be used to improve the accuracy of the spatial distribution of each compound candidate. Examples of the measurement technique or observation technique other than mass spectrometry include a morphological observation method using a common type of optical microscope, a method in which a stained or fluorescently labeled sample is observed with an optical or fluorescent microscope, an infrared microscope imaging method, a laser Raman spectroscopic microscope imaging method, and a method which determines the distribution of the degree of absorption or intensity of radiation of microwaves (e.g. X-rays).

Specifically, as one mode of the imaging mass spectrometer according to the present invention, the spectrum classifier may include a narrowing processor configured to narrow down measurement points to be subjected to the multivariate analysis, using distribution information of a compound contained in the sample, the distribution information acquired by a measurement technique or observation technique different from mass spectrometry.

For example, consider the case where the target compound is one of the various metabolites produced in vivo from a specific kind of drug, and image information showing the distribution information of a metabolite contained in a sample has already been obtained by a measurement method or observation method different from mass spectrometry. The narrowing processor refers to the image information showing the distribution of the metabolite and excludes measurement points at which the metabolite in question is not present from the target of the multivariate analysis. This reduces the amount of data as compared to the case where the data acquired for the entire measurement area are subjected to the multivariate analysis. The period of time required for the multivariate analysis is thereby shortened, so that the process result can be quickly obtained.

As another mode of the imaging mass spectrometer according to the present invention, the spectrum classifier may include a narrowing processor configured to separate peaks in a measured spectrum at each measurement point or delete a portion of the peak information, using distribution information of a compound contained in the sample, the distribution information acquired by a measurement technique or observation technique different from mass spectrometry.

For example, consider the case where the target compound is one of the various metabolites produced in vivo from a specific kind of drug, and image information showing the distribution information of a metabolite contained in a sample has already been obtained by a measurement method or observation method different from mass spectrometry. The narrowing processor refers to the image information showing the distribution information of a specific metabolite as well as a known MS/MS spectrum related to that specific metabolite, and deletes the known peak information related to the specific metabolite from a measured spectrum acquired at a measurement point at which the specific metabolite is present. Alternatively, the narrowing processor classifies the peak information in a measured spectrum acquired at a measurement point where the specific metabolite is present into two groups, i.e. the peak information corresponding to the specific metabolite and the remainder of the peak information, and creates a separate spectrum from each group of peak information. This increases the level of quality, or more specifically, the degree of purity of the measured spectrum and improves the accuracy of the multivariate analysis.

Advantageous Effects of Invention

The imaging mass spectrometer according to the present invention can provide users with visualized spatial distribution for each structure of a compound contained in a sample, rather than the spatial distribution for each mass-to-charge ratio as in a conventional device. For example, it can show users spatial distribution for each of a plurality of structural isomers which are identical in mass and yet different from each other in structure. Users can visually understand the spatial distribution of each structural isomer.

DESCRIPTION OF EMBODIMENTS

One embodiment of the imaging mass spectrometer according to the present invention is hereinafter described with reference to the attached drawings.

Figure 1:
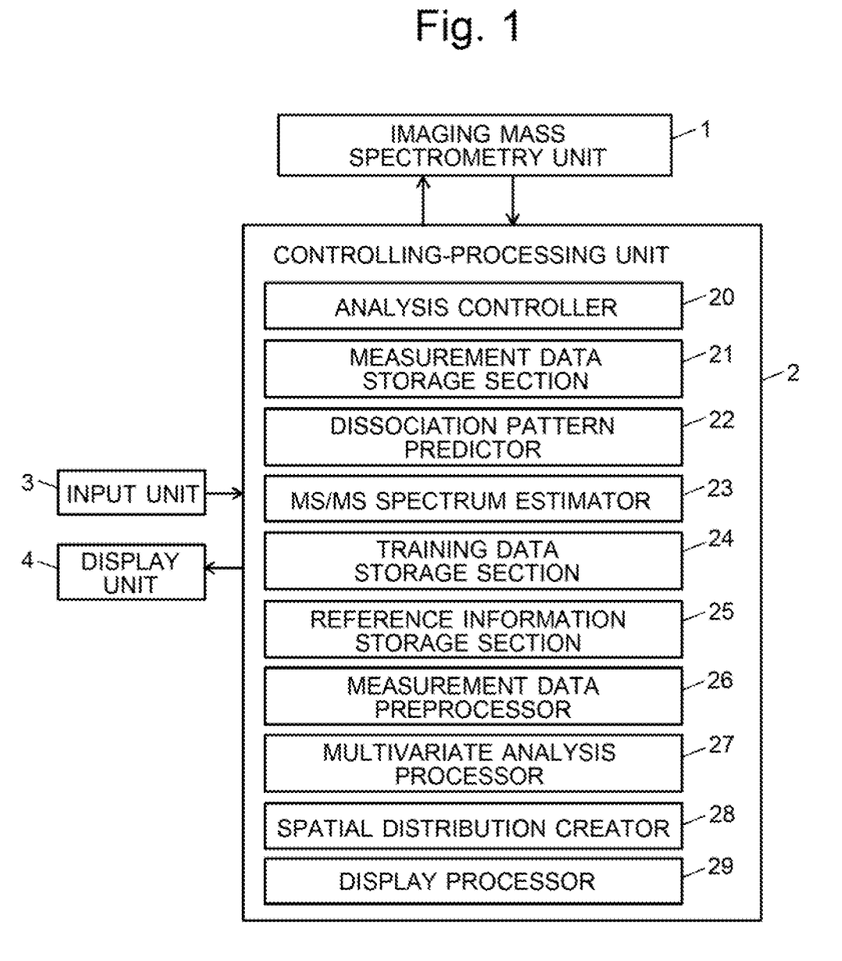
FIG. 1 is a schematic configuration diagram of one embodiment of the imaging mass spectrometer according to the present invention.

FIG. 1 is a schematic configuration diagram of the imaging mass spectrometer according to the present embodiment.

The imaging mass spectrometer according to the present embodiment includes an imaging mass spectrometry unit 1, controlling-processing unit 2, input unit 3 and display unit 4. The input unit 3 and the display unit 4 constitute the user interface.

The imaging mass spectrometry unit 1 includes, for example, a matrix assisted laser desorption/ionization time-of-flight mass spectrometer (MALDI-IT-TOFMS). It acquires mass spectrum data (including $MS^n$ spectrum data) for each measurement point by performing a normal mode of mass spectrometric analysis or $MS^n$ analysis for each of a large number of measurement points (micro areas) within a two-dimensional measurement area on a sample, such as a biological tissue section.

The controlling-processing unit 2 controls the operation of the imaging mass spectrometry unit 1 as well as receives mass spectrum data collected at each measurement point by the imaging mass spectrometry unit 1 under the control of the controlling-processing unit 2, and processes those data by a predetermined method. The controlling-processing unit 2 includes an analysis controller 20, measurement data storage section 21, dissociation pattern predictor 22, MS/MS spectrum estimator 23, teaching data storage section 24, reference information storage section 25, measurement data preprocessor 26, multivariate analysis processor 27, spatial distribution creator 28, display processor 29 and other components as its functional blocks.

The controlling-processing unit 2 is actually a personal computer (or more sophisticated workstation), with the functions of the aforementioned blocks realized by executing, on the computer, dedicated software installed on the same computer. In that case, the input unit 3 is a keyboard and a pointing device, such as a mouse, while the display unit 4 is a display monitor.

Figure 2:
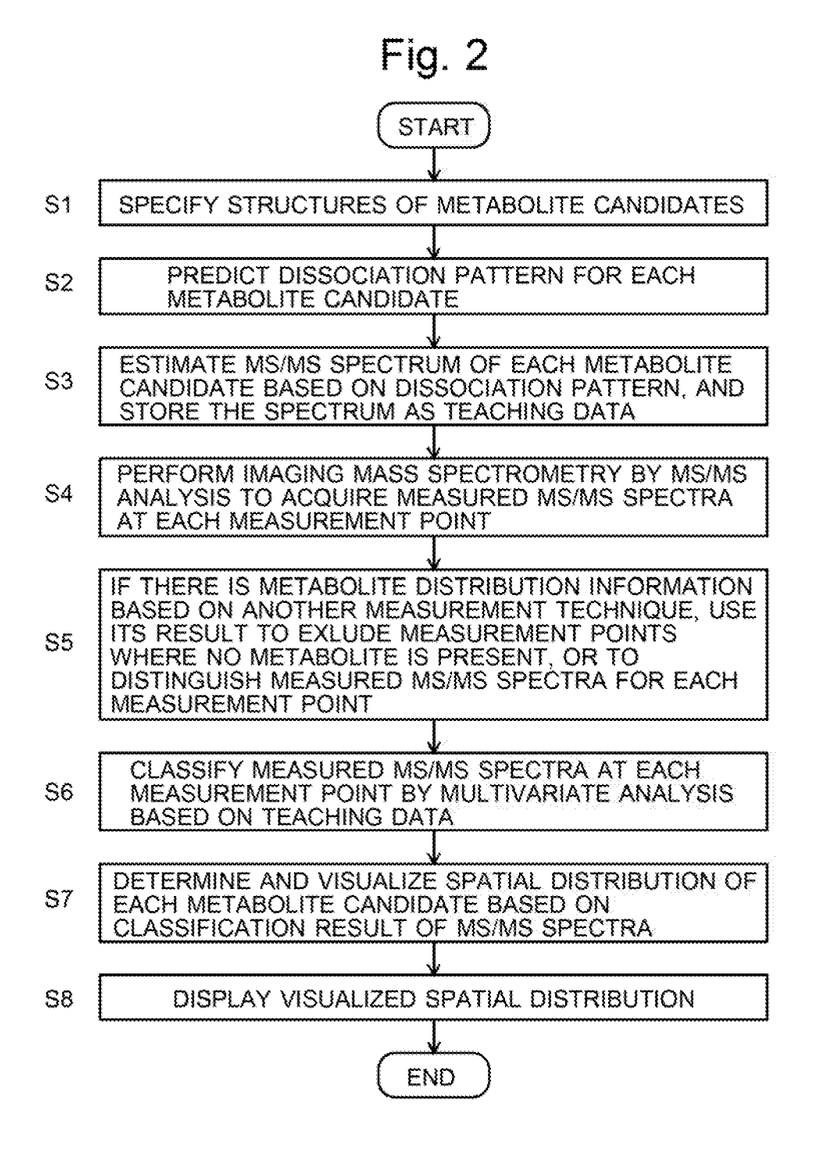
FIG. 2 is a flowchart showing the controlling-processing steps in the process of displaying the spatial distribution of each metabolite candidate in the imaging mass spectrometer according to the present embodiment.

As one example of the analysis using the imaging mass spectrometer according to the present embodiment, the procedure and processing for investigating the spatial distribution of a drug metabolite in a sample (which is a biological tissue section) is hereinafter described with reference to FIGS. 2 and 3A-3D. FIG. 2 is a flowchart of the procedure and processing for investigating the spatial distribution of a drug metabolite. FIGS. 3A-3D are model diagrams illustrating the processing.

In preparation for an analysis, an analysis operator estimates the structures of the candidates of a metabolite contained in the target sample based on the information of the known metabolic pathways and the structural information of the drug. It is hereinafter assumed that there are three metabolite candidates A, B and C. The compounds nominated as the metabolite candidates may have the same mass or different masses.

Additionally, if information (image data) concerning the distribution of a known metabolite on the target sample has already been acquired by a different measurement method or observation method other than the mass spectrometric imaging, the analysis operator instructs the device by an operation from the input unit 3 or other means to read that information and store it in the reference information storage section 25. Examples of the information acquired by a different measurement method or observation method include image data acquired by infrared microscope imaging or laser Raman spectroscopic microscope imaging, image data acquired by taking an image of a stained or fluorescently labeled sample with an optical or fluorescent microscope, and data showing the distribution of the degree of absorption or intensity of radiation of microwaves (e.g. X-rays).

After entering the previously estimated mass information and structural information of the metabolite candidates A, B and C from the input unit 3, the analysis operator performs a predetermined operation (Step S1). For each of the entered metabolite candidates, the dissociation pattern predictor 22 predicts a possible dissociation pattern based on the structural information of the metabolite candidate as well as possible fragment ions which will theoretically be observed as product ions as a result of the dissociation (Step S2). The prediction of the dissociation pattern may be performed using a commercially available software product, such as the "ACD/MS Fragmenter" (Non Patent Literature 2). The pattern can also be predicted by conventionally known theoretical calculations based on the binding energy of the compound.

Based on the predicted result of the dissociation pattern in Step S2, the MS/MS spectrum estimator 23 estimates an MS/MS spectrum for each metabolite candidate. The "MS/MS spectrum" in the present context is a product-ion spectrum covering a predetermined range of mass-to-charge ratios. The theoretical MS/MS spectrum of each metabolite candidate is stored as teaching data in the teaching data storage section 24 (Step S3).

Figures 3A, 3D:
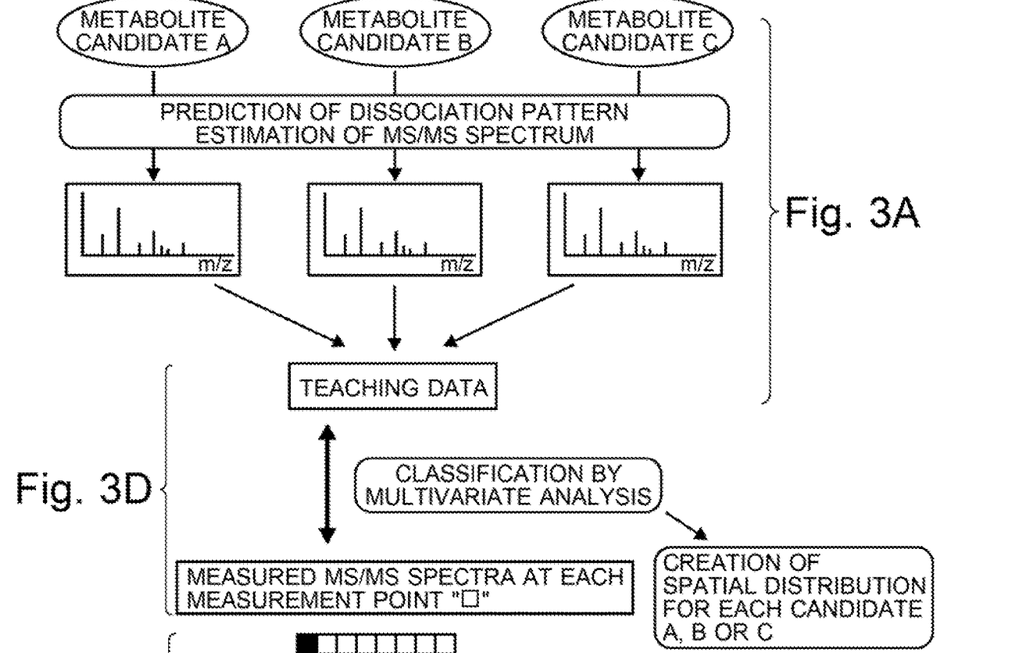
FIGS. 3A-3D are model diagrams for explaining the data processing for acquiring the spatial distribution of each metabolite candidate in the imaging mass spectrometer according to the present embodiment.

In the present case, as shown in FIG. 3A, a set of information showing an MS/MS spectrum is stored as teaching data in the teaching data storage section 24 for each of the three metabolite candidates A, B and C. As will be described later, the items of information practically required in the MS/MS spectrum are the mass-to-charge ratio and signal intensity of each peak. Therefore, the data to be stored in the teaching data storage section 24 only need to include the mass-to-charge ratio and signal intensity of each significant peak observed on the MS/MS spectrum, i.e. a peak that cannot be considered to be a noise peak.

Figure 3B:
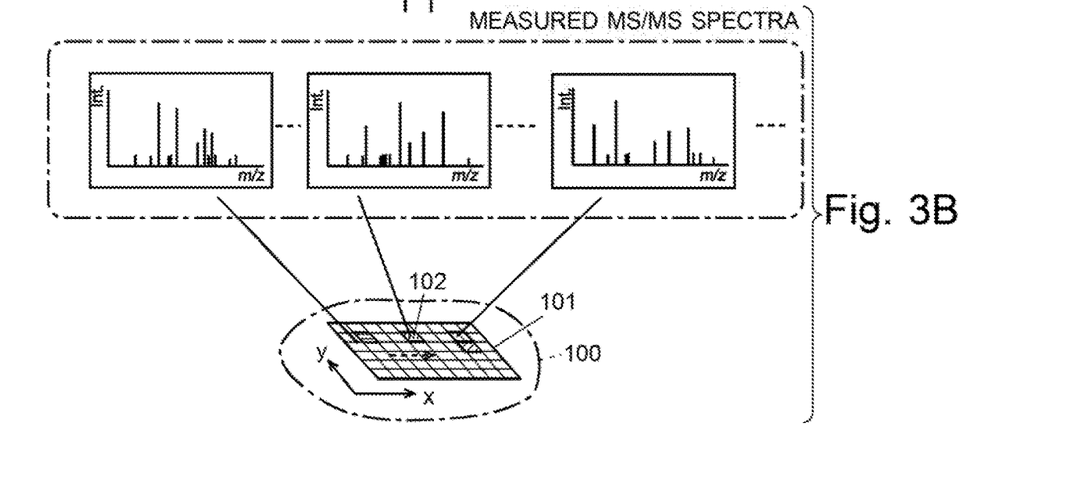

Next, as shown in FIG. 3B, the imaging mass spectrometry unit 1 under the control of the analysis controller 20 performs an MS/MS analysis and acquires a measured mass spectrum for each of the measurement points 102 within a predetermined measurement area 101 on the set sample 100, using a mass-to-charge ratio determined from the mass information of the specified metabolite candidate as the precursor ion (Step S4). The acquired MS/MS spectrum data are sent to the controlling-processing unit 2 and stored in the measurement data storage section 21.

In many cases, the influence of foreign substances is almost completely removed from the MS/MS spectrum. However, a foreign substance whose mass is approximately equal to that of the specified metabolite candidate may happen to be present in the sample, in which case the product ions originating from that foreign substance will also appear on the MS/MS spectrum. Additionally, in the case where the masses of the specified metabolite candidates are the same or extremely close to each other, the product ions originating from those metabolite candidates may be mixed with each other on the MS/MS spectrum. If the previously described reference information is stored in the reference information storage section 25, it may be possible to remove unnecessary data from the measured MS/MS spectrum data by using the reference information. Accordingly, the measurement data preprocessor 26 performs the following processing.

Figure 3C:
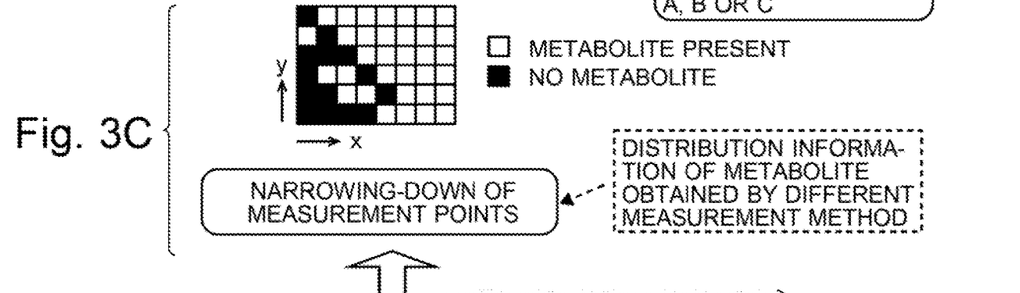

For example, if an area where the metabolite is unlikely to be present has been located within the measurement area based on the reference information, it is preferable to remove the area from the target of the process of determining the spatial distribution of the metabolite. In other words, the following processing should not be performed for the measurement points included within the area where the metabolite is unlikely to be present. FIG. 3C shows one example, in which the measurement points within an area where the metabolite is not present are represented by black squares (■), while the measurement points within an area where the metabolite is present are represented by white squares (□), provided that it is possible to distinguish between the area where the metabolite is not present and the area where the metabolite is present based on a stained image or fluorescent image obtained for the same sample. In this case, it is useless to study the structure of the metabolite for the measurement points represented by the black squares. Therefore, the measured MS/MS spectra acquired for the measurement points represented by the white squares only need to be subjected to the subsequent processing.

Suppose that the spatial distribution of one of the metabolite candidates has been revealed based on the reference information. In that case, if the product ions originating from a plurality of metabolite candidates are observed in a mixed form on an MS/MS spectrum at a measurement point within an area where at least the metabolite candidate in question is present, the MS/MS spectrum can be separated into an MS/MS spectrum of that metabolite candidate and an MS/MS spectrum derived from the other substances. Accordingly, it is preferable to perform a processing for dividing the peaks observed on an MS/MS spectrum into a plurality of MS/MS spectra, or to delete a portion of those peaks (Step S5).

After the processing in Step S5 has been performed as needed, the multivariate analysis processor 27 performs a multivariate analysis on the measured MS/MS spectra at each measurement point, using the MS/MS spectrum of each metabolite candidate stored in the teaching data storage section 24 as the teaching data, to classify the measured MS/MS spectra into groups corresponding to the metabolite candidates (Step S6; see FIG. 3D).

For example, in the previously described case of FIG. 3C, the multivariate analysis only needs to be performed on the measured MS/MS spectra acquired for the measurement points represented by the white squares. It is unnecessary to perform the multivariate analysis on the measured MS/MS spectra acquired for the measurement points represented by the black squares. The multivariate analysis may be performed by any type of technique that can classify data based on teaching data. Typically, the partial least squares (PLS), hierarchical cluster analysis (HCA), k-means cluster analysis, and principal component analysis are useful.

For example, if the PLS is used as the technique for the multivariate analysis, a score is calculated using the technique of PLS for two peak matrices, i.e. a peak matrix based on the peak information in each MS/MS spectrum stored in the teaching data storage section 24 and a peak matrix based on the peak information acquired by performing peak detection on each measured MS/MS spectrum at each measurement point within the measurement area. The PLS score indicates the correlation between the two sets of data respectively included in tse two peak matrices, using the set of data included in one peak matrix as the teaching data. This score is calculated for each measurement point. Accordingly, measurement points which are suitable for classification into one set of teaching data can be selected based on the data which give high PLS scores.

Thus, some of the measurement points within the measurement area are classified into groups corresponding to some of the metabolite candidates. It is naturally possible that one or more specified metabolite candidates are not actually present in the sample. Therefore, the situation in which there is a metabolite candidate with no classified measurement point may possibly occur. Based on the classification result determined in Step S6, the spatial distribution creator 28 creates an image showing the spatial distribution for each metabolite candidate, e.g. for each of the metabolite candidates A, B and C (Step S7). The display processor 29 displays the image created in Step S7 on the screen of the display unit 4 (Step S8).

In the case of determining whether or not a measured MS/MS spectrum is classified into a specific metabolite candidate by the multivariate analysis in Step S6, the classification result is binary information indicating whether or not the measured MS/MS spectrum belongs to the group of the metabolite candidate in question. Accordingly, the image created in Step S7 is an image which shows the range where one metabolite candidate is present. On the other hand, for example, the aforementioned score determined by PLS indicates the probability (reliability) of the presence of one compound candidate. Therefore, based on this score, an image using a gray-scale or color-scale display may be created. The image created in this manner shows the distribution of each metabolite candidate, with the level of the probability of its presence represented by a gray scale or display-color variation. The measurement points removed from the target of the processing in Step S5 can be treated as measurement points at which none of the metabolite candidates is present.

As described to this point, the imaging mass spectrometer according to the present embodiment can display, on the screen of the display unit 4, a spatial distribution image for each structure of the metabolite specified by a user, thereby presenting the image to the user, rather than a spatial distribution image of an ion for each mass-to-charge ratio as in a commonly used device.

Although the example described in the embodiment is concerned with the case of visualizing the spatial distribution of a drug metabolite in a living organism, it is evident that the present technique is applicable to any type of compound and is not limited to metabolites.

In the previous embodiment, measured MS/MS spectra are classified into groups based on the teaching data corresponding to the metabolite candidates. If a piece of information which sufficiently reflects the compound structure has not been acquired by the MS/MS analysis, the dissociating operation may be further repeated to acquire $MS^3$ spectra, or even $MS^4$ spectra, and classify those spectra by multivariate analysis.

In the previous embodiment, MS/MS spectra which are theoretically estimated by the dissociation pattern predictor 22 and the MS/MS spectrum estimator 23 are used as the teaching data for classifying measured MS/MS spectra. Alternatively, MS/MS spectra acquired through previous measurements may be used as the teaching data, i.e. the product-ion spectra to be used as the reference for the multivariate analysis. For example, product-ion spectra for various compounds (metabolites) can be acquired beforehand under standard measurement conditions and compiled into a library in the form of a database. When a metabolite candidate has been specified by an analysis operator, a product-ion spectrum corresponding to that candidate can be read from the library and used as the teaching data. Such a library may be provided by the manufacturer of the device or similar party instead of being created by the user.

It is also evident that the previous embodiment is a mere example of the present invention, and any change, modification, addition or the like appropriately made within the spirit of the present invention in any aspect other than those already described will also fall within the scope of claims of the present application.

REFERENCE SIGNS LIST

1 . . . Imaging Mass Spectrometry Unit
2 . . . Controlling-Processing Unit
20 . . . Analysis Controller
21 . . . Measurement Data Storage Section
22 . . . Dissociation Pattern Predictor
23 . . . MS/MS Spectrum Estimator
24 . . . Teaching Data Storage Section
25 . . . Reference Information Storage Section
26 . . . Measurement Data Preprocessor
27 . . . Multivariate Analysis Processor
28 . . . Spatial Distribution Creator
29 . . . Display Processor
3 . . . Input Unit
4 . . . Display Unit

The invention claimed is:

1. An imaging mass spectrometer equipped with a measurement section capable of performing an $MS^n$ analysis (where n is an integer equal to or greater than two) for each of a plurality of measurement points set within a two-dimensional area on a sample, the imaging mass spectrometer comprising:
   a) a reference spectrum acquirer configured to acquire reference product-ion spectra which respectively correspond to a plurality of compound candidates;
   b) an analysis controller configured to control the measurement section so as to perform $MS^n$ analyses corresponding to mass-to-charge ratios of the plurality of compound candidates and collect spectrum data for each measurement point within a measurement area on a sample;
   c) a spectrum classifier configured to classify measured product-ion spectra obtained under a control of the analysis controller, by a multivariate analysis in which a plurality of reference product-ion spectra acquired by the reference spectrum acquirer are used as teaching data; and
   d) an image creator configured to determine information of the spatial distribution of each compound candidate based on a classification result obtained by the spectrum classifier, and create an image visualizing the spatial distribution.

2. The imaging mass spectrometer according to claim 1, wherein the reference spectrum acquirer is configured to estimate a pattern of dissociation of an ion for each compound candidate based on structures of the plurality of compound candidates, and determine theoretical product-ion spectra to be obtained through the dissociation as the reference product-ion spectra.

3. The imaging mass spectrometer according to claim 1, wherein the spectrum classifier includes a narrowing processor configured to narrow down measurement points to be subjected to the multivariate analysis, using distribution information of a compound contained in the sample, the distribution information acquired by a measurement technique or observation technique different from mass spectrometry.

4. The imaging mass spectrometer according to claim 1, wherein the spectrum classifier includes a narrowing processor configured to separate peaks in a measured product-ion spectrum at each measurement point or delete a portion of the peak information, using distribution information of a compound contained in the sample, the distribution information acquired by a measurement technique or observation technique different from mass spectrometry.

* * * * *